United States Patent
Götte et al.

(10) Patent No.: US 11,911,223 B2
(45) Date of Patent: Feb. 27, 2024

(54) IMAGE BASED ULTRASOUND PROBE CALIBRATION

(71) Applicant: Brainlab AG, Munich (DE)

(72) Inventors: Hubert Götte, Munich (DE); Alfredo Guillermo Illanes Manríquez, Magdeburg (DE); Michael Friebe, Magdeburg (DE); Sathish Balakrishnan, Magdeburg (DE); Prabal Poudel, Magdeburg (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/985,493

(22) PCT Filed: Feb. 23, 2018

(86) PCT No.: PCT/EP2018/054524
§ 371 (c)(1),
(2) Date: Aug. 5, 2020

(87) PCT Pub. No.: WO2019/161914
PCT Pub. Date: Aug. 29, 2019

(65) Prior Publication Data
US 2021/0045719 A1 Feb. 18, 2021

(51) Int. Cl.
*A61B 8/00* (2006.01)
*A61B 90/00* (2016.01)

(52) U.S. Cl.
CPC .............. *A61B 8/58* (2013.01); *A61B 8/4245* (2013.01); *A61B 8/463* (2013.01); *A61B 90/39* (2016.02); *A61B 2090/3925* (2016.02)

(58) Field of Classification Search
CPC ......... A61B 8/58; A61B 8/4245; A61B 8/463; A61B 90/39; A61B 2090/3925; A61B 8/145; A61B 8/587

(Continued)

(56) References Cited

U.S. PATENT DOCUMENTS

2007/0177770 A1* 8/2007 Derchak ................. G06F 21/32
382/115
2008/0269604 A1* 10/2008 Boctor ................. A61B 8/4245
600/437

(Continued)

FOREIGN PATENT DOCUMENTS

CN 105828722 A * 8/2016 ............... A61B 8/12
WO 2013063465 5/2013

(Continued)

OTHER PUBLICATIONS

Wein, Wolfgang, and Ali Khamene. Image-based method for in-vivo freehand ultrasound calibration [online]. Proc. SPIE 6920, Medical Imaging 2008: Ultrasonic Imaging and Signal Processing, Mar. 10, 2008 [retrieved on Dec. 17, 2020], pp. 69200K-1 to 69200K-7. Retrieved from the Internet: < URL/DOI: see Office action>.*

(Continued)

*Primary Examiner* — Joseph M Santos Rodriguez
*Assistant Examiner* — Maria Christina Talty
(74) *Attorney, Agent, or Firm* — Gray Ice Higdon

(57) ABSTRACT

An image-based approach of calibrating an ultrasound-probe is described, wherein at least two ultrasound-images which cross each other are acquired with a tracked ultrasound probe, and wherein the intersection areas of these images, which have been calculated on the basis of the tracked spatial position of the ultrasound probe are checked for similar image content. The grade of similarity gives an indication as to how well the ultrasound probe is calibrated.

18 Claims, 3 Drawing Sheets

(58) Field of Classification Search
USPC .......................................................... 600/437
See application file for complete search history.

(56) References Cited

U.S. PATENT DOCUMENTS

| | | | |
|---|---|---|---|
| 2009/0198134 A1* | 8/2009 | Hashimoto | A61B 8/0883 600/443 |
| 2013/0094769 A1* | 4/2013 | Rezazadeh | G06T 7/0002 382/199 |
| 2013/0144135 A1* | 6/2013 | Mahfouz | A61B 34/10 600/309 |
| 2013/0158403 A1* | 6/2013 | Gottschalk | A61B 8/065 600/447 |
| 2013/0158405 A1* | 6/2013 | Bagge | G01S 7/52068 600/447 |
| 2014/0369557 A1* | 12/2014 | Kayombya | G06T 7/73 382/103 |
| 2015/0139521 A1 | 5/2015 | Kuga | |
| 2015/0216512 A1* | 8/2015 | Luo | A61B 8/4466 600/437 |
| 2016/0228090 A1* | 8/2016 | Boctor | A61B 8/4416 |
| 2018/0132821 A1* | 5/2018 | Dehghan Marvast | A61B 8/58 |

FOREIGN PATENT DOCUMENTS

| | | | | |
|---|---|---|---|---|
| WO | WO-2016055902 A1 * | 4/2016 | | G01S 15/8993 |
| WO | 2019161914 | 8/2019 | | |

OTHER PUBLICATIONS

Mercier, Laurence, et al. A review of calibration techniques for freehand 3-D ultrasound systems [online]. Ultrasound in Medicine & Biology, Apr. 2005 [retrieved on Jan. 12, 2021], vol. 31, No. 4, pp. 449-471. Retrieved from the Internet: < URL: https://www.sciencedirect.com/science/article/pii/S0301562905001195>.*

Carr, Jonathan, et al. Design of a clinical free-hand 3D ultrasound system [online]. Proc. SPIE 3982, Medical Imaging 2000: Ultrasonic Imaging and Signal Processing, Apr. 12, 2000 [retrieved on Jan. 12, 2021], pp. 14-25. Retrieved from the Internet: < URL: see Office action> <DOI: 10.1117/12.382234>.*

Sgourous, Nicholas, et al. Effect of different traversal schemes in integral image coding [online]. Applied Optics, Jul. 1, 2008 [ retrieved on Jan. 13, 2021], vol. 47, No. 19, pp. D28-D37. Retrieved from the Internet: < URL: https://www.osapublishing.org/ao/ abstract.cfm?uri=ao-47-19-D28> <DOI: 10.1364/AO.47.000D28>.*

Y. Ma et al., "Ultrasound calibration using intensity-based image registration: for application in cardiac catherization procedures," Mar. 25, 2008, Medical Imaging 2008: Visualization, Image-Guided Procedures, and Modeling, (Year: 2008).*

International Search Report and Written Opinion issued for PCT/EP2018/054524 dated Dec. 12, 2018.

Madsen et al., "Methods For Non-Linear Least Squares Problems" Informatics and Mathematical Modeling, Technical University of Denmark. 2nd Edition. 30 Pages. Dated Apr. 2004.

* cited by examiner

IMAGE BASED ULTRASOUND PROBE CALIBRATION

FIELD OF THE INVENTION

The present invention relates to a computer-implemented method of calibrating an ultrasound probe, a corresponding computer program, a non-transitory program storage medium storing such a program and a computer for executing the program, as well as a medical system comprising an electronic data storage device and the aforementioned computer.

TECHNICAL BACKGROUND

An ultrasound probe placed at the human body provides insight at a spatially defined image plane. The location of that plane with respect to the probe's housing depends on the probe's internal construction. For use with navigation systems the exact spatial transformation between the image plane and the probe's housing has to be established by a calibration beforehand. Today's calibration procedures utilize a dedicated calibration phantom with well-defined inside structure and a tracked ultrasound probe. The usability of phantoms for calibration is however limited. The phantom's features have to match probe properties as transducer size and imaging depth. The phantom has to be maintained (e.g. cleaned) and quality controlled (e.g. checked for internal geometry and marker location and possible material deterioration) in order to work in a precise and reliable way over its lifetime. Sterility requirements in the operation theatre require cumbersome draping. The need for tracking involves line-of-sight problems between tracking camera and phantom's markers.

The present invention has the object of providing an improved method for calibrating an ultrasound probe, which in particular facilitates a calibration procedure and which also works with simple echogenic structures and simplified phantoms which do not necessarily need to be manufactured with extreme precision.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed invention encompasses an image-based approach of calibrating an ultrasound-probe, wherein at least two ultrasound-images which cross each other are acquired with a tracked ultrasound probe, and wherein the intersection areas of these images, which have been calculated on the basis of the tracked spatial position of the ultrasound probe, are checked for similar image content. The grade of similarity gives an indication as to how well the ultrasound probe is calibrated.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of calibrating an ultrasound probe. The method comprises executing, on at least one processor of at least one computer (for example at least one computer being part of the navigation system), the following exemplary steps which are executed by the at least one processor:

a) image position data is acquired, describing a spatial position in which ultrasound images are expected to be acquired by the ultrasound probe;

b) first image data is acquired, describing a first two-dimensional ultrasound image displaying a structure in a first image plane;

c) second image data is acquired, describing a second two-dimensional ultrasound image displaying the structure in a second image plane intersecting with the first image plane;

d) first intersection data is determined based on the first image data and the image position data, wherein the first intersection data describes content of the first ultrasound image within a linear intersection set defined by the intersecting first and second image planes;

e) second intersection data is determined based on the second image data and the image position data, wherein the second intersection data describes content of the second ultrasound image within the intersection set;

f) similarity data is determined based on the first intersection data and the second intersection data, wherein the similarity data describes a grade of similarity between the contents of the first and second ultrasound images within the intersection set.

The aim of a calibration is to establish the spatial transformation between the spatial position of the ultrasound images, i.e. the video plane and the housing of the probe. The spatial transformation has two components represented by homogeneous matrices. Only one is unknown and thus subject to calibration: The matrix adapterToTransducer represents the position of the transducer in the probe housing. The second matrix transducerToVideo is fully known and provided by the ultrasound device. It represents image scaling properties. The goal of the calibration is to establish adapterToTransducer. It depends on the geometrical position of the transducer inside the probe and the position of the adapter, either being defined by construction or chosen arbitrarily by the user mounting the adapter for each time of use.

Deviation between the video plane and the transducer can occur in any of the six degrees of rotational and translational freedom, i.e. the translational vector components tx, ty, tz and the Euler angles rx, ry, rz. The aim of calibration is to minimize the deviation in all degrees of freedom. The coordinate system transducer can be used to define the x-, y- and z-direction referenced in the following text.

In an example, which allows a full calibration of the ultrasound probe, the method is performed for a plurality of iteration sequences until the grade of similarity is within the defined threshold, and wherein the method further comprises the following steps:

modification data is acquired, describing a positional modification of the image position data;

modified image position data is determined based on the image position data and the modification data, describing, for a subsequent iteration sequence, a positionally modified spatial position in which ultrasound images are expected to be acquired by the ultrasound probe.

As will be explained further below, this allows to verify a correct calibration of the ultrasound probe.

The overall working principle of the inventive method is based on following steps:
1. Acquire set of images
2. Intersect images in space
3. Measure similarity of images at intersections
4. (optional) Change calibration parameters Two application purposes are possible, calibration and verification.

For the purpose of calibration, one-time provision of images with step 1 is followed by steps 2, 3 and 4 being repeated in an optimization loop. Calibration parameters will be changed in the loop to optimize the similarity measure. An optimisation algorithm can be applied, for example a least-square optimisation approach. Specifically, a steepest descend method or Gauß-Newton approach can be applied, or any other applicable approach well known in the art, which are, for example described in a "Methods for non-linear least square problems", $2^{nd}$ Edition, April 2004, K. Madsen, H. B. Nielsen, O. Tingleff, Informatics and Mathematical Modelling, Technical University of Denmark. The optimization runs until the similarity measure fulfils a given quality criteria.

For calibration, the sequence of steps is executed in a loop in order to optimize the calibration parameters. For each sequence in the loop the calibration parameters are changed in order to aim for an improvement of the overall similarity. When a threshold criteria or convergence criteria is met, the optimization loop ends. Criteria can be applied either to overall similarity or calibration parameters. The overall similarity is computed from the similarities in all or only selected intersections. An optional multi-level approach for the calibration is suggested. It can help to find the global optimum of the calibration parameters in less time by using subsequently improved start parameters. It can be applicable, when a calibration with dedicated regions of differing granularity is provided or when down-sampling is used (described further below). In such a multi-level approach, a calibration would be performed on a first set of images to create initial calibration parameters. These images stem from a region of low granularity or a set of images being down-sampled. Afterwards, the found calibration parameters would be used as start values for one or multiple subsequent calibration runs aiming on higher precision. Such a following calibration would work on images from a highly granular region of the object or a set of original images not being down-sampled.

For the purpose of verification, a set of acquired images from step 1 is processed with a one-off execution of steps 2 and 3. The quality measure of the verification is the detected similarity measured across all or a selected subset of the images. Another way of verification of a given calibration is to find the optimal calibration as described above and afterwards calculate the distance between optimal and given calibration parameters. This parameter distances are used as quality measure for the verification.

For verification of an existing calibration, the sequence of steps are being executed once. As a result, the similarity in all intersecting image pairs can be measured and used to calculate a resulting verification quality measure, e.g. as an average over all intersections or over selected ones. Alternatively, a new calibration can be applied and its calculated parameters be compared with the initially given calibration parameters (being either matrix elements or a combination of Euler angles and translational shift parameters) by calculating their distance.

Preferably, the calibration object of which images are acquired is a body of material having echogenic diverse structure. An ultrasound image can be taken with the probe at a certain position and orientation on the object. The probe is equipped with a track able structure. The 6d-position of the adapter in some fixed world coordinate system can be tracked with a tracking system (e.g. via an optical or an electromagnetic tracking system). As the probe is not calibrated yet, the real image plane position and orientation are not known. For acquisition of a second image the probe can be rotated, for example by approx. 90°. This pair of images intersects along a line. Since the position of the image planes is initially not known neither is the position of the intersection line with respect to the world coordinate system.

Thus, an assumed initial calibration is defined which will place the plane at some position and orientation close to the real plane. The acquired image planes are intersected according to their assumed locations and yield a calculated intersection line. Its position is calculated with tracking information and the assumed calibration transformation. When the real intersection is projected back into the calibrated image planes there will be deviation of position and orientation to the calculated intersection line. Depending on the calibration error, the deviation can contain 2d rotational and 2d translational components. In general, real and the calculated lines in both images will deviate from each other by shift and rotation within the image plane.

In each of the images the calculated intersection line runs through and corresponds to a set of pixels. With zero calibration error these pixel sets would be theoretically completely equal to each other (and being the pixel sets at the real intersection line) since they represent the same piece of the imaged object. Due to the calibration error they will differ from each other. This informational divergence will be enhanced when the imaged object contains diverse structure resulting in high image signal entropy.

In practice there will be also some degree of mismatch within the calculated intersection. Even in case of perfect calibration the two images would contain different information at the relevant columns due to changed physical imaging conditions (e.g. speckle, reflections in the object), influence of image processing in the ultrasound device (e.g. cross talk of scan lines, transformation, image post-processing) and differing acquisition aspects (e.g. coupling). Despite these practical limitations, the degree of match between the pixel columns will still be greater the more precise a calibration is provided. In order to measure similarity of pixel columns, the method according to a second aspect of the present invention can be performed. So far, a single intersection was discussed. However, many intersections may be processed and many images may be acquired at various positions and angles. The similarity established in each of the intersections is calculated in an similarity metric and yields an overall similarity measurement value. In order to find the optimum calibration, this overall similarity measurement can be maximized by the calibration loop.

In a further example, the above-described method is therefore performed for a plurality of first acquired images intersecting with a plurality of second acquired images.

A plurality of first images can be acquired, which are rotationally tilted and/or translationally shifted with respect to at least one second image, and/or wherein a plurality of second images is acquired, which are rotationally tilted and/or translationally shifted with respect to at least one first image.

A calibration error can have 6 degrees of freedom (DOF), which can be represented as shifts tx, ty, tz and Euler angles rx, ry and rz. In order to have an effect on similarity, a dedicated moving pattern has to be defined for each degree of freedom or combination. For example, an error in z-direction effects similarity when rotating the probe by 90° around the y-axis as exercised in the examples above. But an error in direction would not affect similarity for this pattern. For calibration and verification it is beneficial to acquire a multitude of images in order to process a multitude of intersections. In practice, a continuous movement along the surface can be applied that contains all necessary patterns varying rotation and translation simultaneously and allows to measure the effect on any of the potential error DOF. The continuous movement can be guided on screen and monitored to catch all necessary information.

In order to provide optimum sensitivity to error, the systematic variation can be guided with support of dedicated software and support a multilevel-approach described further below.

For provision of an automated concept, systematic movements may be applied by a programmed robot. This provides great reproducibility and full control over the movement patterns. Comparable advantages can be exploited when gauges are utilized to guide manually applied movements in a controlled and reproducible way.

Thus, the method described above may comprise the step of determining, based on the image position data and/or acquired tracking data describing the spatial position of the ultrasound probe transducer, control data describing a variation of the spatial position of the ultrasound probe, wherein the control data is either output to a user interface adapted to aid a user in operating a hand-ultrasound probe, or is output to a motorized support structure adapted to control the support structure in operating the ultrasound probe.

The calibration object is a body of echogenic material, structured to provide images with high entropy. It can be implemented in different variations ranging from phantom-like devices to the use of provided anatomical structures. Both sides of the range offer dedicated advantages and disadvantages.

For example, a calibration object designed in a phantom-like fashion offers following advantages:
1) Controlled structure design optimized for high precision of calibration
2) Design of dedicated regions with differing granularity to support multi-level calibration
3) Design of dedicated regions to match probe requirements, e.g. supporting dedicated depths-of-field or providing defined reflection and damping properties
4) Provision of rigid structure to enhance match in image pairs Using anatomical structures instead offers following advantages:
1) No need for providing a dedicated object
2) Simple integration into clinical workflow
3) No need for maintenance Similarity between the intersecting image regions (e.g. pixel columns) can be measured with methods being state-of-the-art, e.g. cross-correlation.

Image Similarity Measures are a widely researched topic and many methods are available to measure similarity of images or image regions. Applicable are known methods like e.g. Normalized Cross Correlation (NCC) or Sum of Squared Differences (SSD, "block matching").

The compared image regions can be down-sampled in order to produce a faster calibration result, e.g. in a multi-level approach. In order to compensate for anisotropic resolution of the ultrasound images in x-, y- and z-direction, dedicated filtering (e.g. Gauss-Filter) can be applied to intersecting images or regions. This filtering will be shaped according to resolution parameters of the individual images at the location of intersection and also be shaped according to the orientation of the intersecting planes.

A further approach disclosed herein to determine similarity of the intersecting image regions is described in the following and in the context of a second aspect of the present invention. Even though the method according to the second aspect preferably supplements the method according to the first aspect, it can generally be used to determine similarity of any images or parts thereof, which are to be compared with each other. Thus, the method described in the following can be seen as a separate invention independent from the method according to the first aspect described above.

In a specific example, determining similarity data involves a computer-implemented method of determining similarity of image content, wherein the method comprises the following steps:

first signal data and second signal data is determined based on a first image, particularly based on the first intersection data, and on a second image, particularly based on the second intersection data, respectively, wherein the signal data describes a one-dimensional signal derived from the image;

first signal band data and second signal band data is determined based on the first signal data and the second signal data, respectively, wherein the signal band data describes a plurality of band signals assigned to different frequency bands, into which a signal is decomposed into;

first modelling data and second modelling data is determined based on the first signal band data and second signal band data, respectively, describing features of a band signal;

similarity data is determined based on the first modelling data and second modelling data, describing a grade of similarity between at least one feature of corresponding band signals derived from of the first image and from the second image, respectively.

In more specific examples, the method according to the second aspect may comprise any of the following features alone or in any meaningful combination:

wherein the image, particularly the intersection data, comprises or is represented by a two-dimensional matrix;

wherein the band signal data comprises or is represented by a one-dimensional vector;

wherein a feature comprises or is represented by a mathematical operation of one or more parameters of a band signal.

wherein the signal data is derived from the image, particularly from the intersection data by scanning the image, particularly the intersection data in a zig-zag-pattern, a spiral-pattern and/or line-by-line-pattern, particularly wherein diverse signal data is derived from the same image, particularly the same intersection data, by applying different scanning techniques;

the first signal data and second signal data is decomposed by applying at least one of a Continuous-Wavelet-Transformation, a Discrete-Wavelet-Transformation, a Fourier-Transformation-based method, an Empirical-Mode-Decomposition;

each of the first signal and second signal is decomposed into at least two, three, or particularly into at least four or more different band signals;

determining first and second modelling data involves using a parametrical autoregressive model, particularly wherein a Power-Spectral-Density is computed for the band signals, particularly wherein determining similarity data involves applying a Pearson-Correlation-Coefficient to compare the Power Spectral-Density.

The concept of the method according to the second aspect is to see an image, for example an ultrasound image as a texture that can be represented as data resulting from a dynamical process which depends on space as an independent variable whose dynamical patterns can characterize such a texture. These dynamics can be modelled using a parametrical approach and the estimated parameters can be taken as a mathematical representation of the texture. Then, two images or two textures can be compared from the parametrical representation, and not from the image itself. The described approach is highly robust to speckle noise presented generally in ultrasound images as well as to low trend intensity inhomogeneity. Additionally, because of the predictive characteristics of such a model representation, better estimations of similarities can be obtained with less data, allowing more localized analysis on the ultrasound image.

In order to follow the dynamical texture characteristics of a two-dimensional "data matrix" image as resulting from a dynamical process the two matrices to be compared are first converted into a one-dimensional "vector" signal. For that different conversion techniques, such as ZigZag or spiral (see FIG. 3) among others, can be used for extracting different signal versions of a matrix. With $n_{I2S}$ being the number of signal versions that are computed from each image data matrix, the first step result in a total of $2n_{I2S}$ output signals.

The second step comprises decomposing each one of the $2n_{I2S}$ signals in several frequency band signals containing each one different aspects of the textures or data matrices that need to be compared. An image texture is composed of several dynamics representing irregularity characteristics of the texture such as smoothness or roughness. Therefore the signals can be decomposed in several dynamics that can represent levels of irregularities presented in the image/texture. For performing this task techniques such as Discrete or Continuous Wavelet Transformation (DWT/CWT), filter banks, Empirical Mode Decomposition (EMD), etc. can be used. This is to separate each signal in different frequency components or scales or modes and then to reconstruct several narrow band signals, from each signal resulting from the Matrix to Signal conversion step, that will contain information of the different levels of texture irregularity. With nbands being the total number of computed narrow band signals then the output of this second step will result in $(n_{I2S} \times n_{bands})$ band signals for each data matrix. Then each one of the $2(n_{I2S} \times n_{bands})$ band signals resulting from the last step is modelled using a parametrical model such as Auto-Regressive model whose parameters will serve for extracting different features representing each signal. The resulting features for a given data matrix are a parameterized way to see the texture of an image as a dynamical process. With nfeatures being the total number of features obtained from each signal belonging to a given matrix, then at the end of the steps of parametrical modeling and feature extraction a total of $(n_{I2S} \times n_{bands} \times n_{features})$ features for each image data matrix are obtained.

It is important to note that $n_{I2S}$, $n_{bands}$, $n_{features}$ can be fully independent and therefore their value can be different. Finally the features belonging to each data matrix are then compared using a correlation-based method such as Pearson coefficient and the final similarity indicator between the two image data matrices is computed as a function of the $(n_{I2S} \times n_{bands} \times n_{features})$ comparison values.

In the following, a specific application of the general concept described above is presented for comparing two image sections in an ultrasound (US) thyroid image:

In a first step four signals for each compared US image are computed. For that the matrices and its transposed are converted into vectors by traversing them in two ways: ZigZag following the matrix rows direction (FIG. 3 left) and spiral (FIG. 3 right). The output of this step result in eight texture signals, four belonging to each compared US image.

Since the eight signals resulting from the conversion step can contain components that are not necessarily oscillatory they are decomposed using scale decomposition instead of frequency Fourier-based decomposition. For that the Continuous Wavelet Transformation (CWT) is used to decompose the signal in three frequency bands representing low, middle and high frequency components (LF, MF and HF). Additionally a fourth frequency band called Total Detrended Frequency Band (TDFB) is computed by using the full band of the signals without the Very Low Frequency components, which correspond to low trend image intensity inhomogeneity.

The resulting 32 narrowband signals are then modelled using a parametrical autoregressive model.

From the estimated AR models the Power Spectral Density for each one of the 32 narrowband signals is then computed. In this example the PSD are used as the only feature extracted from the parametrical model.

The computed PSDs from one US image are then compared with ones of the other US image using a simple Pearson correlation coefficient and then finally the coefficient are sorted in increasing way and finally the average of the sorted coefficient is computed as the final similarity indicator.

In a third aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first and/or according to the second aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first and/or according to the second aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the third aspect therefore may alternatively or additionally relate to a data stream representative of the aforementioned program.

In a fourth aspect, the invention is directed to a non-transitory computer-readable program storage medium on which the program according to the third aspect is stored.

In a fifth aspect, the invention is directed to at least one computer (for example, a computer), comprising at least one processor (for example, a processor) and at least one memory (for example, a memory), wherein the program according to the third aspect is running on the processor or is loaded into the memory, or wherein the at least one computer comprises the computer-readable program storage medium according to the fourth aspect.

In a sixth aspect, the invention is directed to a medical system, comprising:
a) the at least one computer according to the fifth aspect;
b) at least one electronic data storage device storing at least the image position data; and
c) a medical device for carrying out a medical procedure on the patient, wherein the at least one computer is operably coupled to
the at least one electronic data storage device for acquiring, from the at least one data storage device, at least the image position data, and
the medical device for issuing a control signal to the medical device for controlling the operation of the medical device on the basis of the similarity data.

The invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to calibrating an ultrasound probe. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data; a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), X-ray tomography, magnetic resonance tomography (MRT or MRI), conventional X-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
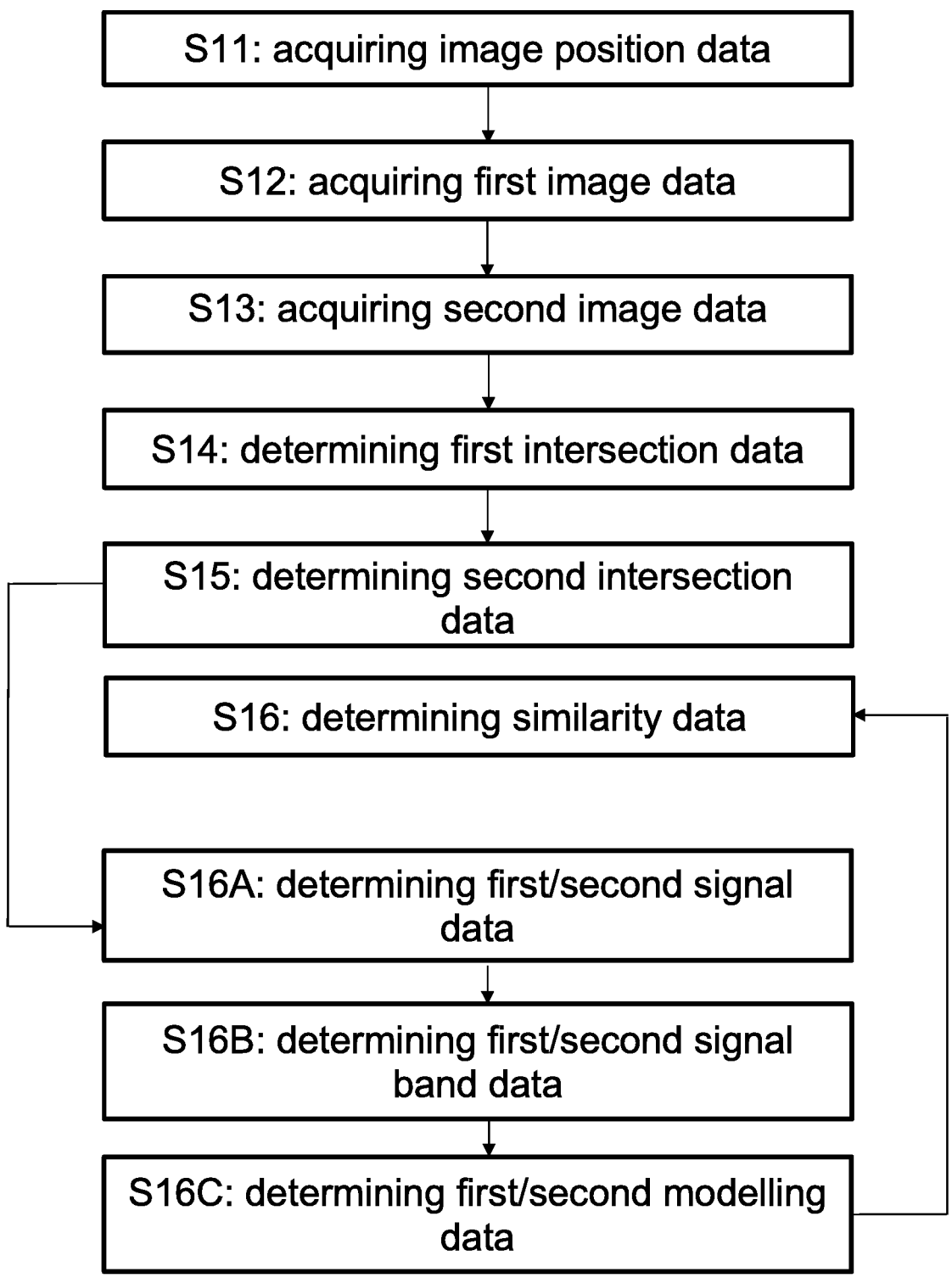
FIG. 1 illustrates the basic steps of the methods according to the first and to the second aspect of the present invention.

FIG. 1 illustrates the basic steps of the method according to the first aspect and to the second aspect.

In steps S11 to S13, at least two intersecting ultrasound-images are acquired, wherein the spatial position of the ultrasound image plane is initially predefined.

Then, the content of each ultrasound image within the image intersection is determined in steps S14 and S15, and compared with each other in step S16. The grade of similarity between the image content indicates how well the ultrasound probe is calibrated.

In this specific example, the method according to the second aspect is used to compare the image content by performing steps S16A to S16C.

Figure 2:
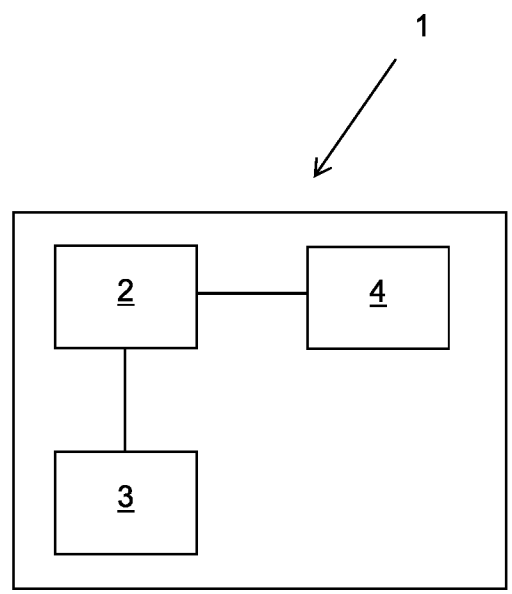
FIG. 2 is a schematic illustration of the system according to the sixth aspect.
Figure 3:
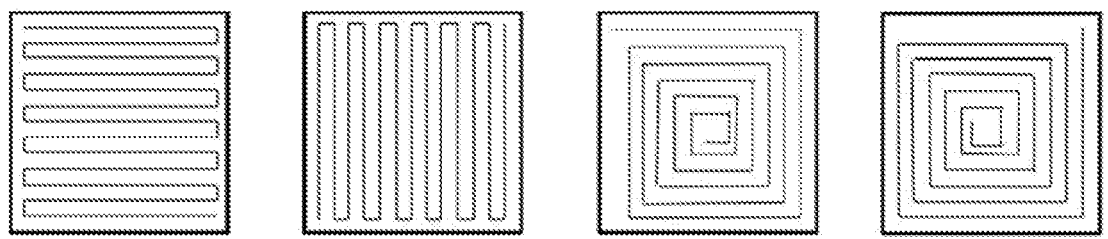
FIG. 3 shows different scanning patterns for deriving a one-dimensional vector signal from a two-dimensional matrix image.

FIG. 2 is a schematic illustration of the medical system 1 according to the sixth aspect. The system is in its entirety identified by reference sign 1 and comprises a computer 2, an electronic data storage device (such as a hard disc) 3 for storing at least the patient data and a medical device 4 (such as a radiation treatment apparatus). The components of the medical system 1 have the functionalities and properties explained above with regard to the fifth aspect of this disclosure.

The invention claimed is:

1. A computer-implemented method of assisting in calibrating an ultrasound probe, comprising:
    acquiring image position data, describing a spatial transformation between a spatial position of ultrasound images acquired by the ultrasound probe and at least one of: a tracked spatial position of the ultrasound probe as determined via a medical tracking system and a spatial position of a housing of the ultrasound probe;
    acquiring first image data, describing a first two-dimensional ultrasound image displaying a structure in a first image plane;
    acquiring second image data, describing a second two-dimensional ultrasound image displaying the structure in a second image plane intersecting with the first image plane along an intersection line;
    determining first intersection data based on the first image data and based on the spatial transformation described by the image position data, wherein the first intersection data describes image content of the first two-dimensional ultrasound image within a first linear intersection set of pixels along the intersection line that is defined by the intersecting first and second image planes;
    determining second intersection data based on the second image data and based on the spatial transformation described by the image position data, wherein the second intersection data describes image content of the second two-dimensional ultrasound image within a second linear intersection set of pixels along the intersection line; and
    determining similarity data based on the first intersection data and the second intersection data,
        wherein the similarity data describes a grade of similarity between the image content of the first two-dimensional ultrasound image within the first linear intersection set of pixels and the image content of the second two-dimensional ultrasound image within the second linear intersection set of pixels.

2. The method according to claim 1, wherein a threshold is defined for the grade of similarity between the image contents of the first two-dimensional ultrasound image within the first linear intersection set of pixels and the second two-dimensional ultrasound images within the second linear intersection set of pixels, wherein a grade of similarity within the threshold indicates that the spatial transformation is acceptable, and a grade of similarity beyond the threshold indicates that the spatial transformation is unacceptable.

3. The method according to claim 2, wherein the method is performed for a plurality of iteration sequences until the grade of similarity is within the threshold, and wherein the method further comprises the following steps:
    acquiring modification data, describing a positional modification of the image position data; and
    determining modified image position data based on the image position data and the modification data, describing, for a subsequent iteration sequence, a positionally modified spatial position in which ultrasound images are expected to be acquired by the ultrasound probe.

4. The method according to claim 3, wherein the modified image position data for which the grade of similarity is within the threshold is stored as image position data for subsequent calibrations of the ultrasound probe.

5. The method according to claim 3, wherein the spatial position in which ultrasound images are expected to be acquired includes a relative spatial position of a transducer of the ultrasound probe with respect to a marker or marker device attached to the ultrasound probe wherein the modification data describes a positional modification of an expected relative position of the transducer with respect to the marker or marker device.

6. The method according to claim 3, wherein the modification data is acquired from an optimisation method which is adapted to increase the grade of similarity between the image content of the first ultrasound image within the first linear intersection set of pixels and the image content of the second ultrasound image within the second linear intersection set of pixels.

7. The method according to claim 1, wherein the method is performed for a plurality of first acquired images intersecting with a plurality of second acquired images.

8. The method according to claim 1, wherein a plurality of first images is acquired, which are rotationally tilted or translationally shifted with respect to at least one second image, and wherein a plurality of second images is acquired, which are rotationally tilted or translationally shifted with respect to at least one first image.

9. The method according to claim 1, further comprising the step of determining, based on the image position data or acquired tracking data describing a spatial position of a transducer of the ultrasound probe, control data describing a variation of the spatial position of the ultrasound probe, wherein the control data is output to a user interface adapted to aid a user in operating the ultrasound probe, or is output to a motorised support structure adapted to control the support structure in operating the ultrasound probe.

10. The method according to claim 1, wherein determining the similarity data involves at least one of:
downsampling the image content described by the first intersection data or by the second intersection data; or
applying a filter to the first intersection data or by the second intersection data.

11. The method according to claim 1, wherein determining the similarity data involves determining similarity between the image contents of the first two-dimensional ultrasound image and the second two-dimensional ultrasound image, comprising the following steps:
determining first signal data and second signal data based on the first two-dimensional ultrasound image and on the second two-dimensional ultrasound image, respectively, wherein the first signal data and the second signal data describes a one-dimensional signal derived from the first two-dimensional ultrasound image and the second two-dimensional ultrasound image, respectively;
determining first signal band data and second signal band data based on the first signal data and the second signal data, respectively, wherein the first signal band data and the second signal band data describes a plurality of band signals assigned to different frequency bands, into which the one-dimensional signal is decomposed into;
determining first modelling data and second modelling data based on the first signal band data and the second signal band data, respectively, describing features of a band signal; and
determining similarity data based on the first modelling data and second modelling data, describing a grade of similarity between at least one feature of corresponding band signals derived from of the first two-dimensional ultrasound image and from the second two-dimensional ultrasound image, respectively.

12. The method according to claim 11, wherein
the first or second intersection data comprises or is represented by a two-dimensional matrix;
at least one of the first signal band data and the second signal band data comprises or is represented by a one-dimensional vector; and
the features of the band signal comprise or are represented by a mathematical operation of one or more parameters of the band signal.

13. The method according to claim 11, wherein
the first or second signal data is derived from the image by scanning the image in a zig-zag-pattern, a spiral-pattern or a line-by-line-pattern;
the first signal data and the second signal data is decomposed by applying at least one of a Continuous-Wavelet-Transformation, a Discrete-Wavelet-Transformation, a Fourier-Transformation-based method, an Empirical-Mode-Decomposition;
each of the first one-dimensional signal and second one-dimensional signal is decomposed into at least two, three, or into at least four or more different band signals; and
determining the first and second modelling data involves using a parametrical autoregressive model.

14. The method of claim 1 wherein
the first image data describes the first two-dimensional ultrasound image which is received directly from the ultrasound probe;
the second image data describes the second two-dimensional ultrasound image which is received directly from the ultrasound probe; and,
wherein the similarity data describes the image contents being confined to the first and second linear intersection sets.

15. A non-transient computer readable storage medium containing program instructions which, when running on at least one processor of a computer, causes the computer to perform a method steps comprising:
acquiring image position data describing a spatial transformation between a spatial position of ultrasound images acquired by an ultrasound probe and at least one of: a tracked spatial position of the ultrasound probe as determined via a medical tracking system and a spatial position of a housing of an ultrasound probe;
acquiring first image data describing a first two-dimensional ultrasound image received from the ultrasound probe and displaying a structure in a first image plane;
acquiring second image data describing a second two-dimensional ultrasound image received from the ultrasound probe and displaying the structure in a second image plane intersecting with the first image plane along an intersection line;
determining first intersection data based on the first image data and based on the spatial transformation described by the image position data, wherein the first intersection data describes image content of the first two-dimensional ultrasound image within a first linear intersection set of pixels along the intersection line that is defined by the intersecting first and second image planes;

determining second intersection data based on the second image data and based on the spatial transformation described by the image position data, wherein the second intersection data describes image content of the second two-dimensional ultrasound image within a second linear intersection set of pixels along the intersection line; and determining similarity data based on the first intersection data and the second intersection data, wherein the similarity data describes a grade of similarity between the image content of the first two-dimensional ultrasound image within the first linear intersection set of pixels and the image content of the second two-dimensional ultrasound image within the second linear intersection set of pixels.

16. A medical system, comprising:

at least one processor of a computer, causing the computer to perform a method having steps comprising:

acquiring image position data describing a spatial transformation between a spatial position ultrasound images acquired by an ultrasound probe and at least one of: a tracked spatial position of the ultrasound probe as determined via a medical tracking system and a spatial position of a housing of an ultrasound probe;

acquiring first image data describing a first two-dimensional ultrasound image received from the ultrasound probe and displaying a structure in a first image plane;

acquiring second image data describing a second two-dimensional ultrasound image received from the ultrasound probe and displaying the structure in a second image plane intersecting with the first image plane along an intersection line;

determining first intersection data based on the first image data and based on the spatial transformation described by the image position data, wherein the first intersection data describes image content of the first two-dimensional ultrasound image within a first linear intersection set of pixels along the intersection line that is defined by the intersecting first and second image planes;

determining second intersection data based on the second image data and based on the spatial transformation described by the image position data, wherein the second intersection data describes image content of the second two-dimensional ultrasound image within a second linear intersection set of pixels along the intersection line;

determining similarity data based on the first intersection data and the second intersection data, wherein the similarity data describes a grade of similarity between the image content of the first two-dimensional ultrasound image within the first linear intersection set of pixels and the image content of the second two-dimensional ultrasound image within the second linear intersection set of pixels;

at least one electronic data storage device storing at least the image position data; and a medical device for carrying out a medical procedure on a patient, wherein the at least one processor of the computer is operably coupled to the at least one electronic data storage device for acquiring, from the at least one electronic data storage device, at least the image position data, and wherein the at least one processor of the computer is operably coupled to the medical device for issuing a control signal to the medical device for controlling the operation of the medical device on a basis of the similarity data.

17. The non-transient computer readable storage medium of claim 15 wherein the first image data describes the first two-dimensional ultrasound image which is received directly from the ultrasound probe;

the second image data describes the second two-dimensional ultrasound image which is received directly from the ultrasound probe; and, wherein the similarity data describes the image contents being confined to the first and second linear intersection sets.

18. The medical system of claim 16 wherein the first image data describes the first two-dimensional ultrasound image which is received directly from the ultrasound probe;

the second image data describes the second two-dimensional ultrasound image which is received directly from the ultrasound probe; and, wherein the similarity data describes the image contents being confined to the first and second linear intersection sets.

* * * * *